(12) United States Patent
Hirasawa et al.

(10) Patent No.: US 8,883,443 B2
(45) Date of Patent: Nov. 11, 2014

(54) METHOD FOR PRODUCING ZEAXANTHIN BY FERMENTATION

(75) Inventors: Kazuaki Hirasawa, Tokyo (JP); Hiroshi Satoh, Tokyo (JP); Hisashi Yoneda, Tokyo (JP); Tetsuhisa Yata, Tokyo (JP); Mitsutoshi Azuma, Tokyo (JP)

(73) Assignee: JX Nippon Oil & Energy Corporation (JP)

( * ) Notice: Subject to any disclaimer, the term of this patent is extended or adjusted under 35 U.S.C. 154(b) by 25 days.

(21) Appl. No.: 13/637,698

(22) PCT Filed: Mar. 29, 2011

(86) PCT No.: PCT/JP2011/057794
§ 371 (c)(1),
(2), (4) Date: Sep. 27, 2012

(87) PCT Pub. No.: WO2011/122616
PCT Pub. Date: Oct. 6, 2011

(65) Prior Publication Data
US 2013/0030218 A1    Jan. 31, 2013

(30) Foreign Application Priority Data

Mar. 30, 2010 (JP) .................................. 2010-079415

(51) Int. Cl.
*C12P 23/00* (2006.01)

(52) U.S. Cl.
USPC ........................................................ 435/67

(58) Field of Classification Search
USPC .................................. 435/67, 252.1; 568/816
See application file for complete search history.

(56) References Cited

U.S. PATENT DOCUMENTS

| | | | |
|---|---|---|---|
| 3,841,967 A | 10/1974 | Dasek et al. | |
| 5,308,759 A | 5/1994 | Gierhart | |
| 5,427,783 A | 6/1995 | Gierhart | |
| 6,087,152 A | 7/2000 | Hohmann et al. | |
| 6,124,113 A | 9/2000 | Hohmann et al. | |
| 6,207,409 B1 | 3/2001 | Hohmann et al. | |
| 6,613,543 B2 | 9/2003 | Hohmann et al. | |
| 8,030,022 B2 * | 10/2011 | Tanaka et al. | 435/67 |
| 2003/0044886 A1 * | 3/2003 | Tsubokura et al. | 435/67 |
| 2003/0108598 A1 * | 6/2003 | Garnett et al. | 424/451 |
| 2007/0105189 A1 | 5/2007 | Tsubokura et al. | |
| 2008/0107060 A1 | 5/2008 | Andou et al. | |
| 2012/0059192 A1 * | 3/2012 | Hirasawa et al. | 568/324 |
| 2013/0012594 A1 * | 1/2013 | Hirasawa et al. | 514/691 |

FOREIGN PATENT DOCUMENTS

| | | |
|---|---|---|
| JP | 48049989 | 7/1973 |
| JP | 05508532 | 12/1993 |
| JP | 9023888 | 1/1997 |
| JP | 2005087097 | 4/2005 |
| JP | 2008118525 | 5/2008 |
| JP | 2010172293 | 8/2010 |
| JP | 2010193865 | 9/2010 |
| WO | 2010/044469 | 4/2010 |

OTHER PUBLICATIONS

Berry A. et al. *Paracoccus zeaxanthinifaciens* sp. nov. A Zeaxanthin Producing Bacterium. Int J of Systematic and Evolutionary Microbiology 53:231-238, 2003.*
International Preliminary Report on Patentability (Oct. 2, 2012), PCT/JP2011/057794, filed Mar. 29, 2011.
English translation (Nov. 13, 2012) of International Preliminary Report on Patentability (Oct. 2, 2012) PCT/JP2011/057794, filed Mar. 29, 2011.

* cited by examiner

*Primary Examiner* — Ralph Gitomer
(74) *Attorney, Agent, or Firm* — McCarter & English

(57) ABSTRACT

A method for microbiologically producing zeaxanthin at high concentration and low cost while suppressing production of gluconic acid is presented. Specifically, a method for producing carotenoids containing zeaxanthin by culturing a bacterium producing carotenoids containing zeaxanthin in a medium containing biotin is provided.

11 Claims, No Drawings

METHOD FOR PRODUCING ZEAXANTHIN BY FERMENTATION

CROSS-REFERENCE TO RELATED APPLICATIONS

This application is a national stage application filed under 35 U.S.C. §371 of PCT/JP2011/078559, filed Dec. 9, 2011, which claims the benefit of Japanese Patent Application No. 2010-079415, filed Mar. 30, 2010.

SEQUENCE LISTING

The Sequence Listing associated with this application is filed in electronic format via EFS-Web and hereby is incorporated by reference into the specification. The name of the text file containing the Sequence Listing is Replacement_Seq_List 119244-00031_ST25.txt. The size of the text file is 2.43 KB, and the text file was created on Jun. 12, 2014.

TECHNICAL FIELD

The present invention relates to a method for producing carotenoids, containing zeaxanthin, by microorganism fermentation.

BACKGROUND ART

Carotenoids are natural pigments that are useful as feed additives, food additives, pharmaceutical agents, and the like. Examples of carotenoids include zeaxanthin, β-carotene, β-cryptoxanthin, astaxanthin, canthaxanthin, lycopene, phoenicoxanthin, adonixanthin, echinenone, asteroidenone, and 3-hydroxyechinenone.

Among carotenoids, zeaxanthin is a natural yellow pigment contained in various plants such as corn, and known to be applied for improving the color tone of egg yolk, meat, or skin of a poultry such as a chicken by being added to feed and be used as a coloring agent for foods. Zeaxanthin also has been reported to have a potent antioxidant function (Non-Patent Document 1) and an anti-tumor effect (Non-Patent Document 2). Further, zeaxanthin is known to be, together with lutein, present in the retina and crystalline lens and involved in the maintenance of eye health (Non-Patent Document 3). Due to these physiological effects, zeaxanthin is useful as a material for health foods, cosmetics, or pharmaceuticals.

β-Cryptoxanthin is contained in citrus fruits, known to have an anti-tumor effect (Non-Patent Document 2), and reported to have an effect of preventing osteoporosis (Non-Patent Document 4). β-Cryptoxanthin is applied for a health food material or a feed additive.

β-Carotene has provitamin A function and antioxidant function and is widely used as a feed additive, food additive, natural coloring agent, or the like.

When zeaxanthin, β-cryptoxanthin, or β-carotene is added to feed for a poultry such as a chicken and the feed is given to the poultry, it accumulates in egg yolk. Since carotenoids have the above physiological effects, eggs in which these carotenoids have accumulated in egg yolk are useful as functional eggs.

Known examples of methods for producing zeaxanthin include chemical synthesis using, as a raw material, an optically active hydroxyketone obtained by asymmetric reduction of oxoisophorone (Non-Patent Document 5) and extraction from corn seeds. Extraction of zeaxanthin from marigold is also known (Patent Document 1); however, a marigold-derived carotenoids mainly contain lutein and have a reduced content of zeaxanthin.

Known examples of microorganisms that produce zeaxanthin include *Spirulina* algae (Patent Document 2), *Nannochloris* spp. microalgae (Patent Document 3), *Flexibacter* spp. bacteria (Patent Document 4), *Alteromonas* spp. bacteria (Patent Document 5), *Flavobacterium* spp. bacteria, and *Agrobacterium aurantiacum* (Non-Patent Document 6). In addition, among bacteria belonging to the genus *Paracoccus* known as carotenoid-producing bacteria, the following examples are known as strains that produce zeaxanthin: *Paracoccus zeaxanthinifaciens* strain ATCC 21588 (Non-Patent Document 7), a mutant strain of *Paracoccus carotinifaciens* strain E-396 (Patent Document 6), a mutant strain of *Paracoccus* bacterial strain A-581-1 (Patent Document 6), and a mutant strain of *Paracoccus* bacterial strain (Patent Document 7).

However, the above method for producing zeaxanthin by chemical synthesis have problems in terms of safety because of use of organic solvents and also in terms of the directional trend of recent years toward a natural product. In addition, zeaxanthin production via culturing algae is not practical because of low productivity. Further, extraction of zeaxanthin from a plant has the disadvantages of requiring too much cost because of low zeaxanthin content thereof and difficulty of stable supply due to weather dependency.

Meanwhile, bacteria belonging to the genus *Paracoccus* are advantageous in that proliferation rates thereof are fast, carotenoid productivity thereof is high, and carotenoids can readily be extracted therefrom, etc. However, large amounts of gluconic acid are produced in a culture liquid of such a bacterium, resulting in waste of a carbon source. In addition, accumulated gluconic acid suppresses production of zeaxanthin. Thus, it was impossible to accumulate and produce zeaxanthin at a sufficient concentration in terms of production cost efficiency. Thus, there is need for an inexpensive method for producing zeaxanthin with high safety, by which zeaxanthin can be stably supplied.

CITATION LIST

Patent Literatures

Patent Document 1: JP Patent Application Laid-open Publication No. 8-92205 A (1996)
Patent Document 2: JP Patent Application Laid-open Publication No. 10-155430 A (1998)
Patent Document 3: JP Patent Application Laid-open Publication No. 7-59558 A (1995)
Patent Document 4: JP Patent Application Laid-open Publication No. 5-328978 A (1993)
Patent Document 5: JP Patent Application Laid-open Publication No. 5-49497 A (1993)
Patent Document 6: JP Patent Application Laid-open Publication No. 2005-87097 A
Patent Document 7: JP Patent Application Laid-open Publication No. 2007-151475 A

Non-Patent Literatures

Non-Patent Document 1: Nobuyoshi Shidzu et al., "Fisheries Science," 1996, vol. 62, no. 1, pp. 134-137
Non-Patent Document 2: Tsushima M. et al., "Biol. Pharm. Bull.," 1995, vol. 18, no. 2, pp. 227-233
Non-Patent Document 3: "FOOD Style 21," 1999, vol. 3, no. 3, pp. 50-53

Non-Patent Document 4: Yamaguchi M et al., "ACS Symp Ser (Am Chem Soc)," 2008, vol. 993, pp. 408-418

Non-Patent Document 5: Paust J et al., "Pure Appl. Chem.," 1991, vol. 63, no. 1, pp. 45-58

Non-Patent Document 6: Akihiro Yokoyama and Wataru Miki, "FEMS Microbiology Letters," 1995, vol. 128, pp. 139-144

Non-Patent Document 7: Alan Berry et al., "International Journal of Systematic and Evolutionary Microbiology," 2003, vol. 53, pp. 231-238

SUMMARY OF INVENTION

Problems to be Solved by the Invention

The present invention has been made in view of the above circumstances. An object of the present invention is to provide a method for microbiologically producing zeaxanthin of high concentration at low cost while suppressing production of gluconic acid.

Means for Solving the Problems

As a result of intensive studies in order to achieve the above object, the present inventors have found that production of zeaxanthin of high concentration can be achieved while maintaining the concentration of produced gluconic acid at a low level by adding biotin to a medium during culture of a bacterium that produces zeaxanthin. This has led to the completion of the present invention.

The present invention encompasses the followings.

(1) A method for producing carotenoids containing zeaxanthin, the method including a step of culturing a bacterium producing carotenoids containing zeaxanthin in a medium containing biotin, wherein a concentration of produced gluconic acid and a concentration of produced zeaxanthin in a culture liquid after the end of culture are lower and higher, respectively, than those in a culture liquid after the end of culture in a biotin-free medium.

(2) The method according to (1), wherein the concentration of produced gluconic acid in the culture liquid after the end of culture is 80 g/L or less.

(3) The method according to (1), wherein an amount of produced gluconic acid in the culture liquid after the end of culture accounts for 30% (w/w) or less of an amount of consumed carbon source.

(4) The method according to (1), wherein the produced carotenoids include β-cryptoxanthin.

(5) The method according to (1), wherein the produced carotenoids include β-carotene.

(6) The method according to (1), wherein the concentration of biotin in the medium is from 0.001 mg/L to 50 mg/L.

(7) The method according to (1), wherein a zeaxanthin content in the culture liquid after the end of culture based on dry cells is 2 mg/g or more.

(8) The method according to (1), wherein a poly-β-hydroxybutyrate (PHB) content in the culture liquid after the end of culture based on dry cells is 30% (w/w) or less.

(9) The method according to (1), wherein the bacterium is a bacterium belonging to the genus *Paracoccus*.

(10) The method according to (1), wherein the bacterium is of a mutant strain capable of producing zeaxanthin obtained by subjecting an astaxanthin-producing bacterium belonging to the genus *Paracoccus* to mutation treatment.

(11) The method according to (1), wherein the bacterium is of a mutant strain having lowered gluconic acid production ability compared with the parent strain.

(12) The method according to (1), wherein the bacterium is of a mutant strain having lowered PHB production ability compared with the parent strain.

(13) The method according to (1), wherein the bacterium is a bacterium in which the nucleotide sequence of DNA corresponding to 16S ribosomal RNA is substantially homologous to the nucleotide sequence shown in SEQ ID NO: 1.

(14) The method according to (1), wherein the bacterium is of a mutant strain from strain E-396 (FERM BP-4283) or A-581-1 (FERM BP-4671).

(15) A carotenoid composition including carotenoids containing zeaxanthin produced by the method according to (1), wherein a PHB content in the culture liquid after the end of culture based on dry cells is 30% (w/w) or less.

(16) A dry cell composition including carotenoids containing zeaxanthin produced by drying the culture liquid obtained by the method according to (1), wherein the zeaxanthin content in the composition is 2 mg/g or more.

This description includes part or all of the contents as disclosed in the description of Japanese Patent Application No. 2010-079415, which is a priority document of the present application.

Effects of the Invention

According to the present invention, zeaxanthin of high concentration can be microbiologically produced at low cost while keeping the gluconic acid concentration at a low level. Carotenoids, containing zeaxanthin, produced by the present invention are useful as feed and food materials.

EMBODIMENTS FOR CARRYING OUT THE INVENTION

Hereinafter, the present invention will be described in more detail. The scope of the present invention should not be limited by the descriptions below and may appropriately be modified and carried out apart from the following illustrative embodiments without departing from the spirit of the present invention.

The present invention relates to a method for producing carotenoids, containing zeaxanthin, by culturing a bacterium that produces carotenoids, containing zeaxanthin (hereinafter occasionally referred to as a "carotenoid-producing bacterium" or "zeaxanthin-producing bacterium") in a medium containing biotin (hereinafter referred to as "the method of the present invention"). According to the method of the present invention, a concentration of produced gluconic acid and a concentration of produced zeaxanthin in a culture liquid after the end of culture are lower and higher, respectively, than those in a culture liquid obtained using a similar carotenoid-producing bacterium after the end of culture in a biotin-free medium. According to the method of the present invention, it becomes possible to produce zeaxanthin of high concentration at low cost by adding biotin to a medium while suppressing the concentration of produced gluconic acid.

A bacterium used in the method of the present invention is not limited as long as it produces zeaxanthin. However, bacteria belonging to the genus *Paracoccus* are preferably used. Among the bacteria belonging to the genus *Paracoccus*, *Paracoccus carotinifaciens*, *Paracoccus marcusii*, *Paracoccus haeundaensis*, and *Paracoccus zeaxanthinifaciens* are preferably used, and *Paracoccus carotinifaciens* is particularly preferably used. Specific examples of bacterial strains belonging to the genus *Paracoccus* include *Paracoccus carotinifaciens* strain E-396 (FERM BP-4283) and *Paracoccus* bacterial strain A-581-1 (FERM BP-4671). Also, a mutant strain capable of more selectively producing zeaxanthin than the parent strain obtained by subjecting any of the above-mentioned strains to mutation may preferably be used in the method of the present invention. Another example of a specific bacterial strain of a zeaxanthin-producing bacterium is *Paracoccus zeaxanthinifaciens* strain ATCC 21588 (Non-Patent Document 7).

As a zeaxanthin-producing bacterium, a bacterium in which the nucleotide sequence of DNA corresponding to 16S ribosomal RNA is substantially homologous to the nucleotide sequence of the strain E-396 shown in SEQ ID NO: 1 is preferably used. The phrase "substantially homologous" as used herein means that homology between nucleotide sequences is preferably 95% or more, more preferably 96% or more, further preferably 97% or more, particularly preferably 98% or more, and most preferably 99% or more in consideration of error frequency and the like in DNA sequencing. Homology can be determined using, for example, the Clustal W gene analysis software.

The phrase "the nucleotide sequence of DNA corresponding to 16S ribosomal RNA" means a nucleotide sequence obtained by substituting U (uracil) in the nucleotide sequence of 16S ribosomal RNA with T (thymine).

Classification of microorganisms based on the homology of the nucleotide sequence of 16S ribosomal RNA is recently becoming the mainstream. Since conventional classification of microorganisms is based on conventionally known mycological properties such as mobility, auxotrophy, and sugar utilization, microorganisms may incorrectly be classified when there happens a change in the characteristics or the like due to spontaneous mutation. On the other hand, since the nucleotide sequence of 16S ribosomal RNA is fairly genetically stable, classification based on its homology greatly improves reliability of the classification as compared to conventional classification methods.

Homologies between the nucleotide sequence of 16S ribosomal RNA of *Paracoccus carotinifaciens* strain E-396 and the nucleotide sequences of 16S ribosomal RNAs of other carotenoid-producing bacteria, i.e., *Paracoccus marcusii* strain DSM 11574 (International Journal of Systematic Bacteriology (1998), 48, 543-548), *Paracoccus* bacterial strain N-81106 (JP Patent Application Laid-open Publication No. 2007-244205 A), *Paracoccus haeundaensis* strain BC 74171 (Jae Hyung Lee et al., "International Journal of Systematic and Evolutionary Microbiology," 2004, vol. 54, pp. 1699-1702), *Paracoccus* bacterial strain A-581-1, *Paracoccus zeaxanthinifaciens* strain ATCC 21588, and *Paracoccus* sp. strain PC-1 (WO2005/118812) are 99.7%, 99.7%, 99.6%, 99.4%, 95.7%, and 95.4%, respectively, showing that these strains are extremely close strains in terms of taxonomy. Accordingly, these strains may be regarded as making one group of carotenoid-producing bacteria.

A mutant strain capable of more selectively producing zeaxanthin than the parent strain obtained by subjecting an astaxanthin-producing bacterium to mutation treatment can be used in the method of the present invention. Examples of such a mutant strain include mutant strains disclosed in Patent Documents 6 and 7.

A method for obtaining a mutant strain capable of selectively producing zeaxanthin by subjecting an astaxanthin-producing bacterium to mutation treatment is exemplified below.

A parent strain for mutation may be any bacterium as long as the bacterium produces astaxanthin; however, bacteria belonging to the genus *Paracoccus* are preferably used. Among astaxanthin-producing bacteria belonging to the genus *Paracoccus*, *Paracoccus carotinifaciens*, *Paracoccus marcusii*, and *Paracoccus haeundaensis* are preferably used, and *Paracoccus carotinifaciens* is particularly preferably used. Specific examples of *Paracoccus* bacterial strains include *Paracoccus carotinifaciens* strain E-396 (FERM BP-4283) and *Paracoccus* bacterial strain A-581-1 (FERM BP-4671). Also, mutant strains having improved astaxanthin productivity obtained by subjecting these strains to mutation may preferably be used as parent strains. As an astaxanthin-producing bacterium used as a parent strain for mutation, a bacterium in which the nucleotide sequence of DNA corresponding to 16S ribosomal RNA is substantially homologous to the nucleotide sequence of the strain E-396 shown in SEQ ID NO: 1 is preferably used. The phrase "substantially homologous" as used herein means that homology between nucleotide sequences is preferably 95% or more, more preferably 96% or more, further preferably 97% or more, particularly preferably 98% or more, and most preferably 99% or more in consideration of error frequency and the like in DNA sequencing.

A method for subjecting the astaxanthin-producing microorganism to mutation treatment is not particularly limited as long as the method induces the mutation thereof. For example, chemical methods using a mutagen such as N-methyl-N'-nitro-N-nitrosoguanidine (NTG) or ethyl methanesulfonate (EMS), physical methods such as ultraviolet irradiation or X-ray irradiation, and biological methods such as genetic recombination or transposon can be used. Alternatively, mutation may be naturally occurring spontaneous mutation. The mutation treatment may be carried out once or more, for example, in a manner such that the mutation treatment is performed to provide mutants having high astaxanthin production ability which are further subjected to mutation treatment. In the present invention, colonies may be formed on a solid medium after the mutation treatment, followed by randomly selecting colonies. However, colonies taking on yellow to orange color can be selected in comparison with red to reddish orange colonies of the parent strain for the improvement of selection efficiency.

A method for selecting a mutant strain having a significantly high proportion of the amount of produced zeaxanthin to the whole amount of carotenoids from among mutant strains obtained by subjecting astaxanthin-producing bacteria to mutation treatment is established by analyzing carotenoid compounds in the culture liquids obtained by culturing mutant strains. For example, such a method is described as follows. Specifically, culture is carried out in a medium containing components that are necessary for the growth of a zeaxanthin-producing bacterium and the production of a carotenoid compound. The culture method may be any method including shaking culture using test tubes, flasks, and the like, aeration agitation culture, or the like. The method for analyzing carotenoid compounds may be any method as long as the method can separate and detect carotenoid compounds; for example, high performance liquid chromatography, thin layer chromatography, or paper chromatography may be used. According to the present invention, the zeaxanthin-producing bacterium may be obtained by screening for a mutant strain having a high proportion of the amount of produced zeaxanthin to the whole amount of carotenoids. Here, the term "the whole amount of carotenoids" refers to the total amount of carotenoid compounds such as astaxanthin, canthaxanthin, adonixanthin, β-carotene, echinenone, zeaxanthin, β-cryptoxanthin, 3-hydroxyechinenone, asteroidenone, and adonirubin. Minimum criteria for the selection require that the proportion of the amount of produced zeaxanthin in a mutant strain is higher than that in the parent strain before mutation treatment, however, a mutant strain in which the proportion of the amount of produced zeaxanthin to the whole amount of produced carotenoids is preferably 20% (w/w) or more, more preferably 40% (w/w) or more, and further preferably 60% (w/w) or more may be selected.

In the method of the present invention, a zeaxanthin-producing bacterium may be subjected to mutation treatment, a mutant strain having improved zeaxanthin productivity compared with the parent strain may be selected, and the thus obtained mutant may be used. A specific example of a method for obtaining a mutant strain having improved zeaxanthin productivity is a method wherein mutation treatment is carried out in the above manner, colonies taking deep orange color on an agar medium are selected, each mutant strain is cultured in a test tube, a flask, or the like, the amount of zeaxanthin is quantified, and a mutant strain with a high zeaxanthin production concentration is selected.

In the method of the present invention, a mutant strain having lowered PHB (poly-$\beta$-hydroxybutyrate) production ability compared with the parent strain may be used. For example, such a mutant strain can be induced from any of the above-described *Paracoccus* bacterial strains. It is known that zeaxanthin-producing bacteria intracellularly accumulate PHB as a storage carbon source. Accumulation of PHB causes waste of the carbon source in a medium. Thus, it is preferable to minimize accumulation of PHB for production cost reduction. That is, it is effective to obtain a mutant strain characterized by accumulation of a small amount of PHB or no accumulation of PHB by performing mutation treatment and screening. A specific example of a method for obtaining a strain characterized by low PHB production is a method in which mutation treatment is performed in the manner described above, each mutant strain is cultured using a test tube, a flask, an agar medium, or the like, the amount of PHB is quantified, and a mutant strain characterized by low PHB production is selected.

In the method of the present invention, a mutant strain having lowered gluconic acid production ability compared with the parent strain may also be used. For example, such a mutant strain can be induced from the above-described *Paracoccus* bacterial strains. Production of gluconic acid results in waste of the carbon source in a medium. In addition, accumulation of large amounts of gluconic acid causes inhibition of bacterial growth or carotenoid production. Thus, it is effective to minimize gluconic acid production for carotenoid production. A specific example of a method for obtaining a strain characterized by low gluconic acid production is a method in which mutation treatment is performed in the manner described above, each mutant strain is cultured in a test tube, a flask, or the like, the pH of each resulting culture liquid is measured, mutant strains for which a small decrease in the pH of the culture liquid has been confirmed are selected, and the amount of gluconic acid in the culture liquid of each selected mutant strain is quantified, and a mutant strain characterized by low gluconic acid production is selected.

Mutant strains to which preferable properties have been imparted, such as the mutant strain having improved zeaxanthin productivity, the mutant strain having lowered PHB production ability, and the mutant strain having lowered gluconic acid production ability described above, may be separately obtained. Alternatively, mutation treatment and screening can be repeated in order to obtain a mutant strain having two or more such properties. It is also possible to obtain a mutant strain to which two or more properties have been imparted by carrying out a combination of two or more types of screening methods with a single mutation treatment. A mutant strain having two or more preferable properties may also be used in the method of the present invention.

Strain E-396 exemplified as a carotenoid-producing bacterium used in the method of the present invention has been deposited as international deposition with the International Patent Organism Depositary (IPOD), the National Institute of Advanced Industrial Science and Technology (AIST) as described below.

International Depositary Authority:
 The International Patent Organism Depositary (IPOD), the National Institute of Advanced Industrial Science and Technology (AIST) (the former National Institute of Bioscience and Human-Technology, the Agency of Industrial Science and Technology, the Ministry of International Trade and Industry)
 Tsukuba Central 6, 1-1-1 Higashi, Tsukuba, Ibaraki, 305-8566, Japan Identification Indication: E-396
Accession No.: FERM BP-4283
Date of the original deposit: Apr. 27, 1993

In addition, strain A-581-1 exemplified as another carotenoid-producing bacterium used in the method of the present invention has been deposited as international deposition with the International Patent Organism Depositary (IPOD), the National Institute of Advanced Industrial Science and Technology (AIST) as described below.

International Depositary Authority:
 The International Patent Organism Depositary (IPOD), the National Institute of Advanced Industrial Science and Technology (AIST) (the former National Institute of Bioscience and Human-Technology, the Agency of Industrial Science and Technology, the Ministry of International Trade and Industry)
 Tsukuba Central 6, 1-1-1 Higashi, Tsukuba, Ibaraki, 305-8566, Japan Identification Indication: A-581-1
Accession No.: FERM BP-4671
Date of the original deposit: May 20, 1994

Examples of carotenoids other than zeaxanthin produced by the method of the present invention include, but are not particularly limited to, $\beta$-carotene, $\beta$-cryptoxanthin, astaxanthin, canthaxanthin, adonixanthin, phoenicoxanthin, echinenone, asteroidenone, 3-hydroxyechinenone, and lycopene. Preferable examples include $\beta$-carotene and $\beta$-cryptoxanthin. One type of carotenoid or a combination of multiple types of carotenoids may be produced according to the method of the present invention.

A method for culturing the above bacteria according to the method of the present invention is described below.

A medium for producing zeaxanthin used for culture in the method of the present invention may be any medium as long as the medium contains biotin and allows the growth of a zeaxanthin-producing bacterium and the production of zeaxanthin. Preferably, a medium containing a carbon source, a nitrogen source, an inorganic salt, and if necessary, a vitamin or the like is used. That is, biotin is added to a medium that allows the growth of a zeaxanthin-producing bacterium and the production of zeaxanthin according to the method of the present invention.

Examples of carbon sources include: sugars such as glucose, sucrose, lactose, fructose, trehalose, mannose, mannitol, and maltose; organic acids such as acetic acid, fumaric acid, citric acid, propionic acid, malic acid, malonic acid, and pyruvic acid; alcohols such as ethanol, propanol, butanol, pentanol, hexanol, isobutanol, and glycerol; and oils and fats such as soybean oil, rice bran oil, olive oil, corn oil, sesame oil, and linseed oil, among which glucose or sucrose is preferably used. One or more types of these carbon sources can be used. The amount of a carbon source added to a preculture medium (starting medium) differs depending on the type of the carbon source, and may adequately be adjusted, but is usually from 1 to 100 g and preferably from 2 to 50 g per 1 L of the medium. The carbon source can be added not only to the starting medium but may also preferably be additionally supplied during culture in a sequential or continuous manner.

Examples of inorganic nitrogen sources include: ammonium salts such as ammonium nitrate, ammonium sulfate, ammonium chloride, and ammonium phosphate; nitrates such as potassium nitrate; ammonia; and urea. One or more types of these inorganic nitrogen sources are used. The amount of an inorganic nitrogen source added differs depending on the type of the nitrogen source and may appropriately be adjusted, but it is usually from 0.1 g to 20 g and preferably from 0.2 to 10 g per 1 L of the medium.

Examples of organic nitrogen sources include corn steep liquor (including filtrated products), pharmamedia, soybean meal, soybean flour, peanut meal, monosodium glutamate, Distillers' solubles, and dried yeast. Among them, one or more types of organic nitrogen sources are used. The concentration of an organic nitrogen source added differs depending on the type of the nitrogen source and may appropriately be adjusted, but it is usually from 0 to 80 g/L and preferably from 0 to 30 g/L in the medium.

The inorganic nitrogen source and the organic nitrogen source are usually added to the starting medium; however, they may also preferably be additionally supplied in a sequential or continuous manner.

Examples of inorganic salts include: phosphates such as potassium dihydrogen phosphate, dipotassium hydrogen phosphate, and disodium hydrogen phosphate; magnesium salts such as magnesium sulfate and magnesium chloride; iron salts such as iron sulfate and iron chloride; calcium salts such as calcium chloride and calcium carbonate; sodium salts such as sodium carbonate and sodium chloride; manganese salts such as manganese sulfate; cobalt salts such as cobalt chloride; copper salts such as copper sulfate; zinc salts such as zinc sulfate; molybdenum salts such as sodium molybdate; nickel salts such as nickel sulfate; selenium salts such as sodium selenate; boric acid; and potassium iodide. One or more types of these inorganic salts are used. The amount of an inorganic salt added differs depending on the type of the inorganic salt and may appropriately be adjusted, but it is usually from 0.0001 to 15 g per 1 L of the medium. The concentration of a phosphate, a magnesium salt, a calcium salt, a sodium salt, or an iron salt is preferably from 0.02 to 15 g/L in the medium. When a manganese salt, a cobalt salt, a copper salt, a zinc salt, a molybdenum salt, a nickel salt, a selenium salt, boric acid, potassium iodide, or the like is added, the concentration thereof is preferably from 0.1 to 15 mg/L. The inorganic salt is usually added to the starting medium; however, it may also be additionally supplied in a sequential or continuous manner.

Examples of vitamins other than biotin which can be used include cyanocobalamin, riboflavin, pantothenic acid, pyridoxine, thiamine, ascorbic acid, folic acid, niacin, p-aminobenzoic acid, inositol, and choline. The proportion of a vitamin added differs depending on the type of the vitamin and may appropriately be adjusted, but it is usually from 0.001 to 1000 mg and preferably from 0.01 to 100 mg per 1 L of the medium. The vitamin is usually added to the starting medium; however, it may additionally be added in a sequential or continuous manner.

The method of the present invention has a feature of culturing a zeaxanthin-producing bacterium in a medium to which biotin has been added. Zeaxanthin of high concentration can be produced while keeping gluconic acid concentration at a low level by culturing a zeaxanthin-producing bacterium in a medium to which biotin has been added.

Biotin used in the method of the present invention may be DL-biotin or D-biotin. D-biotin is preferably used. Biotin is usually added to the starting medium; however, biotin may be added intermittently or continuously during culture. Alternatively, biotin may be added to the starting medium and further added intermittently or continuously during culture. Biotin may be mixed with a basal medium and then the medium may be sterilized. Alternatively, biotin may separately be sterilized and then added to a basal medium. The method for sterilizing biotin is not particularly limited and thus may be heat sterilization or filtration sterilization.

A concentration of biotin added based on the medium does not particularly have a lower limit, however, is preferably 0.001 mg/L or more, more preferably 0.005 mg/L or more, further preferably 0.01 mg/L or more, and particularly preferably 0.02 mg/L or more. There is not particularly an upper limit of the concentration of biotin added, however, concentration thereof is preferably 50 mg/L or less, more preferably 20 mg/L or less, further preferably 10 mg/L or less, particularly preferably 5 mg/L or less, and most preferably 2 mg/L or less.

An antifoamer is preferably used in the method of the present invention in order to prevent formation of bubbles in the culture liquid. Any type of antifoamer can be used as long as the antifoamer can prevent generation of bubbles or disappear the generated bubbles with less inhibition effect on the zeaxanthin-producing bacterium. Examples include alcohol-based antifoamers, polyether-based antifoamers, ester-based antifoamers, fatty acid-based antifoamers, silicone-based antifoamers, and sulfonic acid-based antifoamers. The amount of an antifoamer added differs depending on the type of the antifoamer and may appropriately be adjusted, but it is usually from 0.01 g to 10 g per 1 L of the medium.

The antifoamer is usually added to the starting medium prior to sterilization. It may also be additionally supplied during culture in a continuous or intermittent manner. Examples of a method for adding an antifoamer during culture include: a method in which bubbles are detected using a sensor so as to automatically add the antifoamer; a method in which the antifoamer is added at constant time intervals using a program timer; and a method in which the antifoamer is mixed with a carbon source, a nitrogen source, a pH adjuster, or the like for feeding such that the mixture is added in response to changes in the growth rate. The antifoamer added to the starting medium may be the same as that added to a culture liquid during culture. Alternatively, different types of antifoamers can be used by making use of the effects thereof.

According to the method of the present invention, pH of the medium at the initiation of culture is adjusted to from 2 to 12, preferably from 6 to 9, and more preferably from 6.5 to 8.0. Preferably, pH within this range is maintained during culture. A preferable method for maintaining pH is a method in which pH of a culture liquid is measured online using a pH electrode provided inside a fermenter to automatically supply alkali. Examples of pH adjusters include an aqueous sodium hydroxide solution, an aqueous potassium hydroxide solution, an aqueous sodium carbonate solution, ammonia water, ammonia gas, an aqueous sulfuric acid solution, and a mixture thereof.

A medium used in the method of the present invention is sterilized before being used for culturing a bacterium. Sterilization can appropriately be carried out by those skilled in the art. For example, the medium in a suitable container can be subjected to heat sterilization in an autoclave. Alternatively, filtration sterilization may be carried out using a sterilizing filter. In another case, sterilization may be carried out by jacket heating and steam injection. If a carbon source such as glucose is subjected to heat sterilization with other medium components, the carbon source turns brownish and thus may be separately sterilized. A vitamin or a minute amount of metal may be subjected to heat sterilization with a basal medium or may be separately sterilized in order to prevent deactivation or precipitation.

According to the method of the present invention, a zeaxanthin-producing bacterium is inoculated into the medium containing biotin prepared as described above and cultured under predetermined conditions. Inoculation is carried out by appropriately growing the bacterial strain by seed culture using a test tube, a flask, a fermenter, or the like, and adding the resulting culture liquid to the medium containing biotin for producing zeaxanthin. The medium used for seed culture is not particularly limited and thus the medium may be a medium containing biotin or a biotin-free medium as long as the medium provides good growth of the zeaxanthin-producing bacterium.

Culture is carried out in a suitable culture container. The culture container can appropriately be selected according to the culture volume, including, for example, a test tube, a flask, a fermenter, or the like.

The temperature for culture is, for example, from 15° C. to 40° C., preferably from 20° C. to 35° C., and more preferably from 25° C. to 32° C. In addition, culture is carried out under aerobic conditions within a culture period of generally from 1 day to 20 days, preferably from 2 to 12 days, more preferably from 3 to 9 days, and particularly preferably from 4 to 7 days.

Examples of aerobic conditions include shaking culture or aeration/agitation culture. Lack of oxygen would negatively influence the growth of the zeaxanthin-producing bacterium or the production of the carotenoid. Thus, continuous monitoring of the dissolved oxygen concentration is preferably carried out using a dissolved oxygen electrode. Thus, it is preferable to control the dissolved oxygen concentration to prevent oxygen depletion. The dissolved oxygen concentration can be controlled by, for example, changing the number of agitation rotations, the aeration volume, internal pressure, the oxygen concentration in an aeration gas.

The dissolved oxygen concentration in a culture liquid is controlled preferably at 0.5 ppm or more, more preferably at 1 ppm or more, and further preferably at 1.5 ppm or more. The upper limit of the dissolved oxygen concentration in a culture liquid that falls within the controlled range is not particularly limited; however, the dissolved oxygen concentration is preferably 8 ppm or less, more preferably 7 ppm or less, further preferably 6 ppm or less, and particularly preferably 5 ppm or less.

A bacterium used in the method of the present invention produces gluconic acid in a culture liquid. If gluconic acid is produced, it causes waste of the carbon source in a medium. In addition, if large amounts of gluconic acid accumulate, it inhibits bacterial growth or carotenoid production. Accordingly, it is effective to minimize gluconic acid production for carotenoid production. According to the method of the present invention, the amount of produced gluconic acid can be reduced by adding biotin to a medium. The gluconic acid concentration in a culture liquid obtained as a final product after the end of culture is preferably 80 g/L or less, more preferably 60 g/L or less, further preferably 40 g/L or less, particularly preferably 20 g/L or less, and even more preferably 10 g/L or less. The lower limit thereof is 0 g/L. In addition, the gluconic acid yield based on the carbon source consumption after the end of culture is preferably 30% (w/w) or less, more preferably 20% (w/w) or less, further preferably 10% (w/w) or less, and particularly preferably 5% (w/w) or less. There is no lower limit thereof.

According to the method of the present invention, production of PHB (poly-β-hydroxybutyrate) can be inhibited by adding biotin to the medium. The PHB content in a culture liquid obtained as a final product after the end of culture based on dry cells is preferably 30% (w/w) or less, more preferably 20% (w/w) or less, further preferably 10% (w/w) or less, and particularly preferably 5% (w/w) or less. The lower limit thereof is 0% (w/w). In particular, the culture liquid in which the PHB content after the end of culture based on dry cells is 30% (w/w) or less can be preferably used as a feed additive.

In the method of the present invention, carotenoids in the culture liquid obtained by culturing the zeaxanthin-producing bacterium or carotenoids extracted from the culture liquid can be quantified by, for example, high performance liquid chromatography.

As described above, the culture liquid obtained by culturing the zeaxanthin-producing bacterium may be directly used as carotenoids. Alternatively, a culture supernatant, a cell concentrate (cell concentrate liquid), wet cells, dry cells, cell lysate, and the like are prepared from the culture liquid, and they can be used as preparations. Further, carotenoids can be obtained from such culture liquid or preparations by extraction, purification, or the like.

The culture supernatant can be prepared by subjecting the culture liquid to centrifugation or filtration so as to remove the bacterial cells from the culture liquid. The cell concentrate (e.g., the cell concentrate liquid) can be obtained by subjecting the culture liquid to centrifugation, membrane filtration concentration, or decantation. The wet cells can be obtained by subjecting the culture liquid to centrifugation or filtration. The dry cells can be obtained by drying the culture liquid, the wet cells, or the cell concentrate (e.g., the cell concentrate liquid) by a general drying method.

pH of the culture liquid is not particularly limited in a step of obtaining the bacterial concentrate. However, the culture liquid may be acidified to promote precipitation of the carotenoids. The acidic condition is not limited as long as pH falls within the acidic range; however, it is preferably pH 6.5 or less, more preferably pH 5.5 or less, and further preferably pH 5.0 or less.

The rate of concentration for the bacterial concentrate from the culture liquid is not particularly limited; however, the rate is preferably from 1.5-fold to 10-fold, and further preferably from 2-fold to 6-fold. The term "the rate of concentration" used herein means that if, for example, the rate of concentration is 2-fold, the volume of the bacterial concentrate becomes half that of the volume of the culture liquid. Concentration is preferably carried out after diluting the culture liquid with water in order to improve an effect of removing unnecessary components in the concentration step. In addition, it is also possible to add water during the concentration operation such as centrifugation, filtration separation, or decantation. Concentration may be carried out again with the addition of water after the previous instance of concentration. The amount of water added for dilution is not limited; however, is preferably from O-fold to 10-fold, more preferably from 0.2-fold to 6-fold, and further preferably from 0.3-fold to 3-fold the volume of the culture liquid.

A centrifuge used for centrifugation may be a continuous- or batch-type centrifuge; however, a continuous-type centrifuge is preferably used. Examples of centrifuges include basket-type, multiple-chamber-type, decanter-type, disc-type (nozzle-type/desludging-type), tubular-type, and rotor-type centrifuges.

A membrane filtration apparatus used for filtration separation may be a static type or cross-flow type membrane filtration apparatus; however, a cross-flow type membrane filtration apparatus is preferably used to facilitate prevention of clogging. Examples of a material used for a membrane include filter paper, filter cloth, chemical fiber, and ceramic.

Drying is not particularly limited; however, examples thereof include spray drying, fluidized drying, spray fluidized granulation drying, drum drying, and lyophilization. Preferably, a dried bacterium is pulverized so as to be finely powdered following drying. Pulverization is not particularly limited; however, examples thereof include beater milling, hammer milling, ball milling, and bead milling.

The thus obtained dried bacterium composition containing carotenoids can be directly used as an additive for feed or food.

The zeaxanthin content in the dried bacterium composition is preferably 2 mg/g or more, more preferably 4 mg/g or more, and further preferably 6 mg/g or more. The upper limit thereof is not particularly limited; however, the content is preferably 50 mg/g or less, more preferably 40 mg/g or less, and further preferably 30 mg/g or less.

A method for collecting the carotenoids from the above culture liquid or preparations is not particularly limited in the method of the present invention. It may be any method that allows efficient and stable collection of the carotenoids. Those skilled in the art can carry out such a method by selecting an adequate technique from among known extraction and purification techniques.

Prior to extraction, the culture liquid or preparations may be subjected to at least one treatment selected from among a chemical treatment using an alkaline reagent or a surfactant, a biochemical treatment using a lytic enzyme, a lipid-degrading enzyme, a protease, or the like, and a physical treatment such as ultrasonication or pulverization.

For instance, if the carotenoids are extracted from the culture liquid or preparations, solvents used for extraction and washing are not particularly limited. However, examples thereof include lower alcohols (e.g., methanol, ethanol, and isopropanol), acetone, tetrahydrofuran, methyl ethyl ketone, methyl isobutyl ketone, dichloromethane, chloroform, dimethylformamide, and dimethylsulphoxide.

If it is desired to minimize the risk of oxidation of the carotenoids during the extraction operation, extraction can be carried out under an inert gas atmosphere such as a nitrogen gas atmosphere. It is also possible to select an antioxidant used for pharmaceutical agents or foods and add it to an extraction solvent according to need. Alternatively, a combination of such treatments may be carried out.

In addition, extraction may be carried out under conditions including shielding light in order to minimize the risk of degradation of the carotenoids due to light.

The thus obtained extract can be directly used as carotenoids or may be further purified before use.

A method for separating the bacterium and the like from the extract (e.g., the liquid extract) obtained after the extraction operation is not particularly limited. However, examples thereof include membrane filtration, centrifugation, and decantation.

In general, heating and/or vacuum concentration, crystallization, or the like can be used as a method for obtaining a carotenoid precipitate from the extract. In addition to such a method, a carotenoid pigment may be separated without being concentrated by low-temperature precipitation of the carotenoid pigment or precipitation using an acid/alkali agent or a different salt. For industrial use, the extract is desirably subjected to crystallization.

If necessary, the resulting carotenoid precipitate may be subjected to suspension/agitation for washing using a small amount of a solvent such as lower alcohol.

A washing means is not particularly limited, while practically preferable methods include a method in which filtration is performed following suspension/agitation and a method in which a liquid is passed through from above the precipitate.

The culture liquid, preparation, extract, and purified product obtained in the above manner may be used alone as carotenoids or may be mixed and used at given proportions.

EXAMPLES

Hereinafter, the present invention will be described specifically by way of examples, although the scope of the present invention should not be limited to the following examples.

Carotenoids were quantified in the examples as described below using high performance liquid chromatography (HPLC).

Two columns (Inertsil SIL-100A, 5 μm (φ: 4.6×250 mm) (GL Sciences)) were used in tandem. Elution was performed by running an n-hexane/tetrahydrofuran/methanol mixture solution (40:20:1) as a mobile phase at a rate of 1.0 mL per minute at a constant temperature around room temperature. For measurement, samples dissolved in tetrahydrofuran were 100-fold diluted with the mobile phase and 20 μL of the resultant was injected. The column eluent was detected at a wavelength of 470 nm. Furthermore, zeaxanthin (produced by EXTRASYNTHESE) (Cat. No. 0307 S) was used as a standard preparation for quantification. The concentration of zeaxanthin in the standard solution was determined according to the following formula after measuring: (A): the absorbance of the standard solution at 453 nm and; (B): the area percentage (%) of the zeaxanthin peak obtained upon HPLC analysis under the above conditions.

$$\text{Concentration of zeaxanthin(mg/L)} = A/2327 \times B \times 100$$

Example 1

*Paracoccus carotinifaciens* strain E-396 (FERM BP-4283) was subjected to mutation treatment using N-methyl-N'-nitro-N-nitrosoguanidine, and colonies taking on yellow to orange color were selected. The carotenoid concentrations in the culture liquids of the selected strains were measured. Accordingly, the ZX-3 mutant strain having high zeaxanthin production ability was selected.

A hundred milliliter of a medium (having the following composition: sucrose: 30 g/L; corn steep liquor: 30 g/L; potassium dihydrogen phosphate: 1.5 g/L; disodium hydrogen phosphate dodecahydrate: 3.8 g/L; calcium chloride dihydrate: 5.0 g/L; magnesium sulfate heptahydrate: 0.7 g/L; and iron sulfate heptahydrate: 0.3 g/L (pH 7.2)) was poured into a 500-ml cotton-plugged conical flask and sterilized in an autoclave at 121° C. for 20 minutes to prepare seven flasks of the medium for seeding.

Next, 2.0 L of a medium (having the following composition: glucose: 20 g/L; corn steep liquor: 30 g/L; ammonium sulfate: 0.5 g/L; potassium dihydrogen phosphate: 2.25 g/L; disodium hydrogen phosphate dodecahydrate: 5.7 g/L; calcium chloride dihydrate: 0.1 g/L; magnesium sulfate heptahydrate: 0.5 g/L; iron sulfate heptahydrate: 5 g/L; and an alcohol-based antifoamer: 0.5 g/L) was poured into a 5-L fermenter. Seven fermenters were prepared in such a manner.

D-biotin was added to the fermenters to result in concentrations of 0, 0.001, 0.01, 0.1, 1.0, 10, and 50 mg/L, respectively, and each resultant was sterilized in an autoclave at 121° C. for 40 minutes.

A platinum loopful of *Paracoccus* zeaxanthin-producing bacterial strain ZX-3 described above was inoculated into the medium for seeding in each flask prepared above, followed by rotary shaking culture at 100 rpm and 29° C. for 2 days. Subsequently, the resulting culture liquids (80 mL each) were separately introduced into the fermenters as described above for aerobic culture at 29° C. with an aeration volume of 1 vvm for 120 hours. pH was continuously controlled with 15% ammonia water so as to be maintained at 7.1 during culture. Glucose was continuously fed to prevent depletion of glucose. In addition, the number of agitation rotations was changed (the lowest number of agitation rotations: 100 rpm) to maintain the dissolved oxygen concentration in each culture liquid at 2 ppm in the intermediate phase of culture (i.e., a period during which oxygen consumption by a microorganism becomes most active). Once bubble formation was detected with a bubble sensor, an alcohol-based antifoamer was automatically added to prevent bubble formation.

The carotenoid concentration, the gluconic acid concentration, and the PHB content based on dry cells in each culture liquid at the end of culture were measured. Table 1 shows the results. The zeaxanthin concentration and the gluconic acid concentration in each experimental plot to which biotin had been added at 0.001 to 50 mg/L were found to be higher and lower, respectively, than those in a plot to which no biotin had been added. In addition, the term "gluconic acid yield to sugar % (w/w)" used in Table 1 refers to the amount of produced gluconic acid at the end of culture as a percentage of the total amount of consumed glucose.

TABLE 1

| | Biotin concentration mg/L | | | | | | |
|---|---|---|---|---|---|---|---|
| | 0 | 0.001 | 0.01 | 0.1 | 1 | 10 | 50 |
| β-carotene mg/L | 1.9 | 1.8 | 2.0 | 2.0 | 2.3 | 2.1 | 2.3 |
| β-cryptoxanthin mg/L | 0.4 | 0.5 | 0.6 | 0.6 | 0.5 | 0.5 | 0.6 |
| Zeaxanthin mg/L | 14.2 | 23.8 | 25.4 | 27.3 | 28.0 | 27.8 | 27.6 |
| Gluconic acid g/L | 122 | 75 | 58 | 44 | 43 | 24 | 36 |
| Gluconic acid yield to sugar %(w/w) | 49 | 27 | 20 | 17 | 16 | 10 | 13 |
| PHB %(w/w) | 35 | 26 | 22 | 25 | 23 | 27 | 24 |

Example 2

*Paracoccus* bacterial strain A-581-1 (FERM BP-4671) was subjected to mutation treatment using ethyl methanesulfonate, and colonies taking on yellow color were selected. The carotenoids in the culture liquids of the selected strains were measured. Accordingly, the ZX-5 mutant strain producing zeaxanthin was selected.

A hundred milliliter of a medium (having the following composition: sucrose: 30 g/L; corn steep liquor: 30 g/L; potassium dihydrogen phosphate: 1.5 g/L; disodium hydrogen phosphate dodecahydrate: 3.8 g/L; calcium chloride dihydrate: 5.0 g/L; magnesium sulfate heptahydrate: 0.7 g/L; and iron sulfate heptahydrate: 0.3 g/L (pH 7.2)) was poured into a 500-ml cotton-plugged conical flask and sterilized in an autoclave at 121° C. for 20 minutes to prepare two flasks of the medium for seeding.

Next, 2.0 L of a medium (having the following composition: sucrose: 40 g/L; corn steep liquor: 30 g/L; ammonium sulfate: 0.5 g/L; potassium dihydrogen phosphate: 2.25 g/L; disodium hydrogen phosphate dodecahydrate: 5.7 g/L; calcium chloride dihydrate: 0.1 g/L; magnesium sulfate heptahydrate: 0.5 g/L; iron sulfate heptahydrate: 5 g/L; and an alcohol-based antifoamer: 0.5 g/L) was poured into a 5-L fermenter. Two fermenters were prepared in such a manner. D-biotin was added to the fermenters to result in concentrations of 0 and 1.0 mg/L, respectively, and each resultant was sterilized in an autoclave at 121° C. for 30 minutes.

A platinum loopful of *Paracoccus* zeaxanthin-producing bacterial strain ZX-5 described above was inoculated into the medium for seeding in each flask prepared above, followed by rotary shaking culture at 100 rpm and 28° C. for 2 days. Subsequently, the resulting culture liquids (80 mL each) were separately introduced into the fermenters as described above for aerobic culture at 28° C. with an aeration volume of 1 vvm for 140 hours. pH was continuously controlled with 15% ammonia water so as to be maintained at 7.2 during culture. Sucrose was continuously fed to prevent depletion of sucrose. In addition, the number of agitation rotations was changed (the lowest number of agitation rotations: 200 rpm) to maintain the dissolved oxygen concentration in each culture liquid at 1 ppm in the intermediate phase of culture. Once bubble formation was detected with a bubble sensor, a silicone-based antifoamer was automatically added to prevent bubble formation.

The carotenoid concentration, the gluconic acid concentration, and the PHB content based on dry cells in each culture liquid at the end of culture were measured. Table 2 shows the results. The zeaxanthin concentration and the gluconic acid concentration according to the addition of biotin to the medium were higher and lower, respectively, than those measured without the addition of biotin. In addition, the term "gluconic acid yield to sugar % (w/w)" used in Table 2 refers to the amount of produced gluconic acid at the end of culture as a percentage of the total amount of consumed sucrose.

TABLE 2

| Biotin concentration | 0 | 1 mg/L |
|---|---|---|
| β-carotene mg/L | 0.4 | 0.6 |
| β-cryptoxanthin mg/L | 0.1 | 0.2 |
| Zeaxanthin mg/L | 5.3 | 9.8 |
| Gluconic acid g/L | 96 | 33 |
| Gluconic acid yield to sugar % (w/w) | 36 | 12 |
| PHB % (w/w) | 25 | 13 |

Example 3

A hundred milliliter of a medium (having the following composition: sucrose: 30 g/L; corn steep liquor: 30 g/L; potassium dihydrogen phosphate: 1.5 g/L; disodium hydrogen phosphate dodecahydrate: 3.8 g/L; calcium chloride dihydrate: 5.0 g/L; magnesium sulfate heptahydrate: 0.7 g/L; and iron sulfate heptahydrate: 0.3 g/L (pH 7.2)) was poured into a 500-ml cotton-plugged conical flask and sterilized in an autoclave at 121° C. for 20 minutes to prepare flasks of the medium for seeding.

Next, 2.0 L of a medium (having the following composition: glucose: 30 g/L; corn steep liquor: 30 g/L; ammonium sulfate: 0.5 g/L; potassium dihydrogen phosphate: 2.25 g/L; disodium hydrogen phosphate dodecahydrate: 5.7 g/L; calcium chloride dihydrate: 0.1 g/L; magnesium sulfate heptahydrate: 0.5 g/L; iron sulfate heptahydrate: 5 g/L; L-monosodium glutamate monohydrate: 6 g/L; and an alcohol-based antifoamer: 0.5 g/L) was poured into a 5-L fermenter. Two fermenters were prepared in such a manner. D-biotin was added to the fermenters to result in concentrations of 0 and 0.1 mg/L, respectively, and each resultant was sterilized in an autoclave at 121° C. for 30 minutes.

A platinum loopful of *Paracoccus zeaxanthinifaciens* strain ATCC 21588 was inoculated into the medium for seeding in the flasks prepared above, followed by rotary shaking culture at 100 rpm and 27° C. for 2 days. Subsequently, the resulting culture liquids (80 mL each) were separately introduced into the fermenters as described above for aerobic culture at 27° C. with an aeration volume of 1 vvm for 120 hours. pH was continuously controlled with 15% ammonia water so as to be maintained at 7.2 during culture. Glucose was continuously fed to prevent depletion of glucose. In addition, the number of agitation rotations was changed (the lowest number of agitation rotations: 100 rpm) to maintain the dissolved oxygen concentration in each culture liquid at 3 ppm in the intermediate phase of culture. Once bubble formation was detected with a bubble sensor, an alcohol-based antifoamer was automatically added to prevent bubble formation.

The carotenoid concentration, the gluconic acid concentration, and the PHB content based on dry cells in each culture liquid at the end of culture were measured. Table 3 shows the results. The zeaxanthin concentration and the gluconic acid concentration according to the addition of biotin to the medium were higher and lower, respectively, than those measured without the addition of biotin. In addition, the term "gluconic acid yield to sugar % (w/w)" used in Table 3 refers to the amount of produced gluconic acid at the end of culture as a percentage of the total amount of consumed glucose.

TABLE 3

| Biotin concentration | 0 | 0.1 mg/L |
|---|---|---|
| β-carotene mg/L | 0.3 | 0.5 |
| β-cryptoxanthin mg/L | 0.1 | 0.2 |
| Zeaxanthin mg/L | 4.4 | 7.3 |
| Gluconic acid g/L | 116 | 61 |
| Gluconic acid yield to sugar % (w/w) | 48 | 26 |
| PHB % (w/w) | 33 | 18 |

Example 4

*Paracoccus carotinifaciens* strain E-396 (PERM BP-4283) was subjected to mutation treatment by ultraviolet irradiation, and colonies taking on yellow to orange color are selected. The selected bacterial strains were cultured in test tubes. Mutant strains for which small decreases in pH of the culture liquids had been confirmed were selected. The gluconic acid concentration and the carotenoid concentration in the test tube culture liquid of each selected mutant strain were measured. Accordingly, the ZX-6 mutant strain having low gluconic acid production ability and high zeaxanthin production ability was selected.

A hundred milliliter of a medium (having the following composition: sucrose: 30 g/L; pharmamedia: 10 g/L; potassium dihydrogen phosphate: 0.8 g/L; dipotassium hydrogen phosphate: 4.2 g/L; calcium chloride dihydrate: 1 g/L; magnesium sulfate heptahydrate: 12 g/L; and iron sulfate heptahydrate: 1 g/L (pH 7.2)) was poured into a 500-ml cotton-plugged conical flask and sterilized in an autoclave at 121° C. for 20 minutes to prepare flasks of the medium for seeding.

Next, 2.0 L of a medium (having the following composition: sucrose: 30 g/L; pharmamedia: 20 g/L; ammonium sulfate: 1.5 g/L; potassium dihydrogen phosphate: 1.5 g/L; disodium hydrogen phosphate dodecahydrate: 3.8 g/L; calcium chloride dihydrate: 0.1 g/L; magnesium sulfate heptahydrate: 4.5 g/L; iron sulfate heptahydrate: 5 g/L; L-monosodium glutamate monohydrate: 6 g/L; and a silicone-based antifoamer: 1 g/L) was poured into a 5-L fermenter. Two fermenters were prepared in such a manner. D-biotin was added to the fermenters to result in concentrations of 0 and 5 mg/L, respectively, and each resultant was sterilized in an autoclave at 121° C. for 30 minutes.

A platinum loopful of *Paracoccus* bacterial strain ZX-6 (which is a zeaxanthin-producing strain having low gluconic acid production ability) selected above was inoculated into the medium for seeding in the flasks prepared above, followed by rotary shaking culture at 100 rpm and 28° C. for 3 days. Subsequently, the resulting culture liquids (80 mL each) were separately introduced into the fermenters as described above for aerobic culture at 28° C. with an aeration volume of 1 vvm for 120 hours. pH was continuously controlled with 25% ammonia water so as to be maintained at 7.2 during culture. Sucrose was continuously fed to prevent depletion of sucrose. In addition, the number of agitation rotations was changed (the lowest number of agitation rotations: 100 rpm) to control the dissolved oxygen concentration in each culture liquid at 4 ppm. A given amount of a fatty acid-based antifoamer was automatically added at constant intervals to prevent bubble formation.

Culture was carried out under the above two conditions. The carotenoid concentration, the gluconic acid concentration, and the PHB content based on dry cells in each culture liquid at the end of culture (120 hours after the initiation of culture) were measured. Table 4 shows the results. The zeaxanthin concentration and the gluconic acid concentration according to the addition of biotin to the medium were higher and lower, respectively, than those measured without the addition of biotin. In addition, the term "gluconic acid yield to sugar % (w/w)" used in Table 4 refers to the amount of produced gluconic acid at the end of culture as a percentage of the total amount of consumed sucrose.

TABLE 4

| Biotin concentration | 0 | 5 mg/L |
|---|---|---|
| β-carotene mg/L | 2.7 | 3.0 |
| β-cryptoxanthin mg/L | 0.9 | 1.2 |
| Zeaxanthin mg/L | 52.5 | 89.1 |
| Gluconic acid g/L | 22 | 0 |
| Gluconic acid yield to sugar % (w/w) | 12 | 0 |
| PHB % (w/w) | 33 | 19 |

Example 5

*Paracoccus carotinifaciens* strain E-396 (FERM BP-4283) was subjected to mutation treatment using N-methyl-N'-nitro-N-nitrosoguanidine, and colonies taking on deep red color were selected. Selected bacterial strains were cultured in test tubes. The PHB content and the carotenoid concentration were measured. Accordingly, the LP-26 mutant strain having low PHB production ability and high astaxanthin production ability was selected. Next, the strain LP-26 was subjected to mutation treatment using N-methyl-N'-nitro-N-nitrosoguanidine, and colonies taking on yellow to orange color were selected. Selected bacterial strains were cultured in test tubes. The PHB content and the carotenoid concentration were measured. Accordingly, the ZXA-7 mutant strain having low PHB production ability and high zeaxanthin production ability was selected.

A hundred milliliter of a medium (having the following composition: sucrose: 20 g/L; corn steep liquor: 5 g/L; potassium dihydrogen phosphate: 0.54 g/L; dipotassium hydrogen phosphate: 2.78 g/L; calcium chloride dihydrate: 5 g/L; magnesium sulfate heptahydrate: 0.7 g/L; and iron sulfate heptahydrate: 3 g/L (pH 7.2)) was poured into a 500-ml cotton-plugged conical flask and sterilized in an autoclave at 121° C. for 20 minutes to prepare flasks of the medium for seeding.

Next, 2.0 L of a medium (having the following composition: glucose 40 g/L; corn steep liquor: 30 g/L; ammonium sulfate: 0.5 g/L; potassium dihydrogen phosphate: 2.25 g/L; disodium hydrogen phosphate dodecahydrate: 5.7 g/L; calcium chloride dihydrate: 0.1 g/L; magnesium sulfate heptahydrate: 0.5 g/L; iron sulfate heptahydrate: 5 g/L; L-monosodium glutamate monohydrate: 6 g/L; and an alcohol-based antifoamer: 0.5 g/L) was poured into a 5-L fermenter. Fermenters were prepared in such a manner. D-biotin was added to the fermenters to result in concentrations of 0 and 0.5 mg/L, respectively, and each resultant was sterilized in an autoclave at 121° C. for 20 minutes.

A platinum loopful of *Paracoccus* bacterial strain ZXA-7 described above having low PHB production ability and high zeaxanthin production ability was inoculated into the medium for seeding in the flasks prepared above, followed by rotary shaking culture at 150 rpm and 27° C. for 2 days. Subsequently, the resulting culture liquids (80 mL each) were separately introduced into the fermenters as described above for aerobic culture at 27° C. with an aeration volume of 1 vvm for 120 hours. pH was continuously controlled with 15% ammonia water so as to be maintained at 7.1 during culture. Glucose was continuously fed to prevent depletion of glucose. In addition, the number of agitation rotations was changed (the lowest number of agitation rotations: 200 rpm) to control the dissolved oxygen concentration in each culture liquid at 6 ppm in the intermediate phase of culture. Once bubble formation was detected with a bubble sensor, an ester-based antifoamer was automatically added to prevent bubble formation.

The carotenoid concentration, the gluconic acid concentration, and the PHB content based on dry cells at the end of culture were measured. Table 5 shows the results. The zeaxanthin productivity according to the addition of biotin to the medium was higher than that measured without the addition of biotin. In addition, the term "gluconic acid yield to sugar % (w/w)" used in Table 5 refers to the amount of produced gluconic acid at the end of culture as a percentage of the total amount of consumed glucose.

TABLE 5

| Biotin concentration | 0 | 0.5 mg/L |
| --- | --- | --- |
| β-carotene mg/L | 14 | 19 |
| β-cryptoxanthin mg/L | 8 | 5 |
| Zeaxanthin mg/L | 182 | 371 |
| Gluconic acid g/L | 84 | 35 |
| Gluconic acid yield to sugar % (w/w) | 34 | 14 |
| PHB % (w/w) | 25 | 5 |

Example 6

Culture of zeaxanthin-producing mutant strain ZX-3 obtained in Example 1 was carried out under the same culture conditions as described in Example 1 with the addition of D-biotin at a concentration of 1 mg/L in a 5 L fermenter for 120 hours.

The pH of the obtained culture liquid was adjusted to 4.5 with sulfuric acid, followed by centrifugation. A suspension was prepared by adding water to the resulting concentrate such that the volume of the suspension became equivalent to the volume of the culture liquid before concentration. Then, centrifugation was performed again. Subsequently, the concentrate was lyophilized to obtain a dried bacterial product.

The zeaxanthin content in the obtained dried bacterial product was 4.1 mg/g. Meanwhile, the zeaxanthin content in a dried bacterial product obtained by carrying out culture and drying in the above manner without the addition of biotin for comparison was 1.3 mg/g.

Example 7

Culture of the ZX-5 zeaxanthin-producing mutant strain obtained in Example 2 was carried out under the same culture conditions as used in Example 2 with the addition of D-biotin at a concentration of 1 mg/L in a 5-L fermenter.

The obtained culture liquid was concentrated 4-fold using a Microza™ microfiltration membrane (Asahi Kasei Chemicals Corporation). Equivalent amount of water was added to the liquid concentrate, followed by further filtration concentration. The obtained concentrate was dried using a drum dryer and thus a dried bacterial product was obtained.

The zeaxanthin content in the obtained dried bacterial product was 2.0 mg/g.

Example 8

The culture liquid obtained in Example 4 by carrying out culture in a 5-L fermenter with the addition of D-biotin at a concentration of 5 mg/L was sterilized at 80° C. for 30 minutes. Subsequently, the pH of the culture liquid was adjusted to 4.6 with the addition of sulfuric acid, and equivalent amount of water was added to the culture liquid. Then, the mixture was centrifuged so as to be concentrated 6-fold.

The zeaxanthin content in a dried bacterial product obtained by drying the concentrate using a spray dryer was 6.6 mg/g.

Example 9

The culture liquid obtained in Example 5 by adding D-biotin to result in a concentration of 0.5 mg/L was subjected to filtration concentration using a cross-flow type ceramic filter so that the concentration increased 2.2 times, and equivalent amount of water was added to the concentrate. The mixture was further filtrated. Accordingly, a liquid concentrate was obtained.

The zeaxanthin content in a dried bacterial product obtained by subjecting the liquid concentrate to drum drying was 24 mg/g.

All publications, patents, and patent applications cited herein are incorporated herein by reference in their entirety.

55

The invention claimed is:

1. A method for producing carotenoids containing zeaxanthin comprising culturing for a period of time a bacterium producing carotenoids containing zeaxanthin in a medium containing biotin, wherein the concentration of biotin in the medium is 0.005 mg/L to 50 mg/L, the concentration of bacterially produced gluconic acid in the culture medium at the end of the culture period is 80 g/L or less, and the zeaxanthin concentration in the culture medium at the end of the culture period is 2 mg/g of dry cells or more.

2. The method according to claim 1, wherein an amount of bacterially produced gluconic acid in the culture medium at the end of the culture period accounts for 30% (w/w) or less of an amount of consumed carbon source.

3. The method according to claim 1, wherein the bacterially produced carotenoids include β-cryptoxanthin.

4. The method according to claim 1, wherein the bacterially produced carotenoids include β-carotene.

5. The method according to claim 1, wherein a poly-β-hydroxybutyrate (PHB) concentration in the culture medium at the end of the culture period based on weight of dry cells is 30% (w/w) or less.

6. The method according to claim 1, wherein the bacterium is a bacterium belonging to the genus *Paracoccus*.

7. The method according to claim 1, wherein the bacterium is a mutant strain capable of producing zeaxanthin obtained by subjecting an astaxanthin-producing bacterium belonging to the genus *Paracoccus* to mutation treatment.

8. The method according to claim 1, wherein the bacterium is a mutant strain having a reduced ability to produce gluconic acid compared with the parent strain.

9. The method according to claim 1, wherein the bacterium is a mutant strain having a reduced ability to produce PHB compared with the parent strain.

10. The method according to claim 1, wherein the bacterium is a bacterium in which the nucleotide sequence of DNA corresponding to 16S ribosomal RNA is substantially homologous to the nucleotide sequence of SEQ ID NO: 1.

11. The method according to claim 1, wherein the bacterium is a mutant strain derived from strain E-396 (FERM BP-4283) or A-581-1 (FERM BP-4671).

* * * * *

SEQUENCE LISTING

<160> NUMBER OF SEQ ID NOS: 1

<210> SEQ ID NO 1
<211> LENGTH: 1452
<212> TYPE: DNA
<213> ORGANISM: Paracoccus carotinifaciens
<220> FEATURE:
<221> NAME/KEY: misc_feature
<222> LOCATION: (1350)..(1350)
<223> OTHER INFORMATION: n is a, c, g, or t

<400> SEQUENCE: 1

```
agtttgatcc tggctcagaa cgaacgctgg cggcaggctt aacacatgca agtcgagcga      60
gaccttcggg tctagcggcg gacgggtgag taacgcgtgg gaacgtgccc ttctctacgg     120
aatagccccg ggaaactggg agtaataccg tatacgccct ttgggggaaa gatttatcgg     180
agaaggatcg gcccgcgttg gattaggtag ttggtggggt aatggcccac caagccgacg     240
atccatagct ggtttgagag gatgatcagc cacactggga ctgagacacg cccagactc     300 ctacgggagg cagcagtggg gaatcttaga caatgggggc aaccctgatc tagccatgcc     360
gcgtgagtga tgaaggcctt agggttgtaa agctctttca gctgggaaga taatgacggt     420
accagcagaa gaagccccgg ctaactccgt gccagcagcc gcggtaatac ggagggggct     480
agcgttgttc ggaattactg ggcgtaaagc gcacgtaggc ggactggaaa gtcagaggtg     540
aaatcccagg gctcaacctt ggaactgcct ttgaaactat cagtctggag ttcgagagag     600
gtgagtggaa ttccgagtgt agaggtgaaa ttcgtagata tcggaggaa caccagtggc     660 gaaggcggct cactggctcg atactgacgc tgaggtgcga aagcgtgggg agcaaacagg     720
attagatacc ctggtagtcc acgccgtaaa cgatgaatgc cagacgtcgg caagcatgct     780
tgtcggtgtc acacctaacg gattaagcat tccgcctggg gagtacggtc gcaagattaa     840
aactcaaagg aattgacggg ggcccgcaca agcggtggag catgtggttt aattcgaagc     900
aacgcgcaga accttaccaa cccttgacat ggcaggaccg ctggagagat tcagctttct     960
cgtaagagac ctgcacacag gtgctgcatg gctgtcgtca gctcgtgtcg tgagatgttc    1020
ggttaagtcc ggcaacgagc gcaacccacg tccctagttg ccagcaattc agttgggaac    1080
tctatggaaa ctgccgatga taagtcggag gaaggtgtgg atgacgtcaa gtcctcatgg    1140
gccttacggg ttgggctaca cacgtgctac aatggtggtg acagtgggtt aatccccaaa    1200
agccatctca gttcggattg tcctctgcaa ctcgagggca tgaagttgga atcgctagta    1260
atcgcggaac agcatgccgc ggtgaatacg ttcccgggcc ttgtacacac cgcccgtcac    1320
accatgggag ttggttctac ccgacgacgn tgcgctaacc ttcgggggc aggcggccac    1380 ggtaggatca gcgactgggg tgaagtcgta acaaggtagc cgtagggaa cctgcggctg    1440 gatcacctcc tt                                                        1452
```